(12) United States Patent
Garcia-Caurel et al.

(10) Patent No.: US 7,298,480 B2
(45) Date of Patent: Nov. 20, 2007

(54) BROADBAND ELLIPSOMETER / POLARIMETER SYSTEM

(75) Inventors: Enric Garcia-Caurel, Paris (FR);
Antonello De Martino, Massy (FR);
Bernard Drevillon, Clamart (FR)

(73) Assignee: Ecole Polytechnique, Palaiseau (FR)

( * ) Notice: Subject to any disclaimer, the term of this patent is extended or adjusted under 35 U.S.C. 154(b) by 104 days.

(21) Appl. No.: 11/315,334

(22) Filed: Dec. 23, 2005

(65) Prior Publication Data
US 2007/0146706 A1    Jun. 28, 2007

(51) Int. Cl.
*G01J 4/00*    (2006.01)
(52) U.S. Cl. ...................................... 356/364
(58) Field of Classification Search .............. None
See application file for complete search history.

(56) References Cited

U.S. PATENT DOCUMENTS

| | | | |
|---|---|---|---|
| 5,396,329 A * | 3/1995 | Kalawsky | 356/364 |
| 5,706,212 A | 1/1998 | Thompson et al. | |
| 6,141,069 A * | 10/2000 | Sharp et al. | 349/98 |
| 6,552,836 B2 * | 4/2003 | Miller | 359/237 |
| 2005/0122514 A1 * | 6/2005 | Jang | 356/365 |

OTHER PUBLICATIONS

Bennett, "A critical evaluation of Rhomb-type quarterwave retarders," *Applied Optics*, vol. 9, No. 9, Sep. 1970, pp. 2123-2129.
Collins et al., "Advances in multichannel ellipsometric techjniques for in-situ and real-time characterization of thin films," *Thin Solid Films*, vol. 38, No. 46, 2004, pp. 469-470.

Filinski et al., "Achromatic phase retarders constructed from right-angle prisms: design," *Applied Optics*, vol. 23, No. 16, Aug. 15, 1984, pp. 2747-2751.
Compain et al., "Broadband division-of-amplitude polarimeter based on uncoated prisms," *Applied Optics*, vol. 37, No. 25, Sep. 1, 1998, pp. 5938-5944.
Compain et al., "General and self-consistent method for the calibration of polarization modulators, polarimeters, and Mueller-matrix ellipsometers," *Applied Optics*, vol. 38, No. 16, Jun. 1, 1999, pp. 3490-3502.
Goldstein, "Mueller matrix dual-rotating retarder polarimeter," *Applied Optics*, vol. 31, No. 31, Nov. 1, 1992, pp. 6676-6683.
De Martino et al., "Optimized Mueller polarimeter with liquid crystals," *Optics Letters*, vol. 28, No. 8, Apr. 15, 2003, pp. 616-618.

(Continued)

*Primary Examiner*—Michael P. Stafira
(74) *Attorney, Agent, or Firm*—Young & Thompson

(57) ABSTRACT

A broadband ellipsometer/polarimeter system for analyzing a sample includes an illumination source emitting a polychromatic light beam, a polarization state generator (PSG) including a fixed linear polarizer and a substantially achromatic retarder mounted on a rotating holder, a sample holder, a polarization state analyser (PSA) including a fixed linear polarizer and a substantially achromatic retarder mounted on a rotating holder, a primary detection system measuring the intensities at each wavelength of the light beam transmitted through the PSA, optics to collimate the beam into the PSG and into the PSA and to focus the beam into the sample surface and the detector. The linear polarizer and achromatic retarder in the PSA are identical to those of the PSG but mounted in a reverse order.

26 Claims, 7 Drawing Sheets

OTHER PUBLICATIONS

Nagib et al., "Optimization of a rhomb-type quarter-wave phase retarder," *Applied Optics*, vol. 34, No. 16, Jun. 1, 1995, pp. 2927-2930.

Rochford et al., "Design and performance of a stable linear retarder," *Applied Optics*, vol. 36, No. 25, Sep. 1, 1997, pp. 6458-6465.

Tyo, "Design of optimal polarimeters: maximization of signal-to-noise ratio and minimization of systematic error," *Applied Optics*, vol. 41, No. 4, Feb. 1, 2002, pp. 619-630.

Sabatke, D.S. et al., "Optimization of retardance for a complete Stokes polarimeter", Optics Letters, vol. 25, No. 11, Jun. 1, 2000, pp. 802-804, XP-02412779.

* cited by examiner

BROADBAND ELLIPSOMETER / POLARIMETER SYSTEM

BACKGROUND OF THE INVENTION

The invention concerns a broadband ellipsometer/polarimeter system and a method of polarimetric measurement of Mueller matrices.

Ellipsometry is a non-destructive characterization technique that measures the change in polarization state of light reflected (or transmitted) by a sample.

The present ellipsometric/polarimetric system contains an excitation section emitting a light beam. Said light beam passes through a polarisation state generator (PSG) and is focused on the sample. After being transmitted, reflected or scattered by the sample, the beam goes through an analysis section containing a polarisation state analyser (PSA) and a detection means.

Such PSG and PSA (which is also called PSD (polarisation state detector)) are described in the document US2004130717.

In a PSG, the light polarization can be modulated by a variety of devices such as discrete components inserted and then removed from the light path {Bickel W. S. et al.; Am. J. Phys 53 (1984) 468}, rotating retardation plates {Goldstein D. H.; Appl. Opt. 31 (1992) 6676}, rotating compensators {Collins R. W. and Koh J.; J. Opt. Soc. A 16, (1999) 1997}, Pockels cells {Delplancke F.; Appl. Opt. 36 (1997) 5388 and Compain E. and Drévillon B.; Rev. Sci. Instrum. 68 (1997) 2671} or photoacoustic modulators {Compain E. and Drévillon B.; Rev. Sci. Instrum. 69, (1998) 1574}.

For PSA, one can use the same devices and a single detector, or a "parallel" analysis of light polarization through polarization-sensitive beamsplitters and simultaneous measurement of the separated beams by several detectors {Azzam R. M. A., Opt. Acta 29 (1982) 685, Brudzewski K.; J. Modern Optics 38 (1991) 889, Khrishnan S.; J. Opt. Soc. Am A 9 (1992) 1615, Compain E. et al., Thin Solid Films 313 (1998)}.

The optical set-up is completed with appropriate optics to collimate the beam into the PSG and into the PSA, and to focus the beam onto the sample surface and on the detector. The PSG generates a set of four independent states of polarization, which after being transformed by the sample, are projected over the PSA to be analyzed. The PSA produces a set of four independent optical configurations to analyze the polarization of the light emerging from the sample for each state that was previously created by the PSG. As a result, a complete measurement run yields a set of 16 independent values that eventually, allows the calculation of the sample Mueller matrix or ellipsometric angles.

To date, several ellipsometers/polarimeters have been described, most of them working in the ultraviolet—visible (UV-VIS) wavelength range (250 to 900 nm) and only a small number working in the mid infrared (IR) (4 to 20 microns) or in the far ultraviolet (FUV) (140 nm-250 nm). This fact can be roughly explained because typically optical elements perform better in the UV-VIS than in the IR of the FUV and also because even though the visible spectral range is relatively narrow, it appears to be sufficient for some applications. However, there is an increasing interest in expanding the measured spectra because FUV and IR have particular advantages. The IR gives unique information about the chemical bonding within a sample, which is inaccessible to the sole UV-VIS. Moreover, because of its longer wavelengths, the IR, is less sensitive than the UV-VIS to surface structures (roughness, inhomogeneity among others). It is also better suited to the analysis of thick films (>several microns) that usually make the interpretation of conventional measurements difficult. On the other hand, the shortness of the FUV wavelengths make it ideal to measure the thickness of very thin films (<a few nm), in addition, the enhanced sensitivity of FUV to small defects and structures in the surface of samples is used for surface state quality control. Finally, it is of general agreement that the wider the measured spectral range, the better is the reliability of the final results.

The preceding arguments prove the necessity for an apparatus providing ellipsometric/polarimetric measurements in spectral ranges as wide as possible. Two particular interesting ranges are the IR range from 4 to 20 microns, and the FUV-NIR from 140 nm to 2 microns.

Briefly, the disclosed apparatus uses polarizers and retarders to create and to analyze the polarization state of a radiation beam. This apparatus is operated by placing the retarders at a set of 16 different orientations with respect to the polarizers, which are kept still.

In order to work in optimal conditions over all the measured spectral range, the polarizers and the retarders used in the instrument must be as much achromatic as possible. The operation mode of the disclosed ellipsometer/polarimeter system imposes an additional constraint to the design of the retarders. They must not deviate the beam even when they are rotated about an axis defined by the direction of the beam. Even if substantially achromatic polarizers can eventually be found commercially this is not always the case for substantially achromatic retarders.

An article of Benett et al. {Appl. Opt., (1970)}, has been used as a reference to select the most adapted types and characteristics of the retarders to be used in the disclosed ellipsometer/polarimeter system. In said article, Bennett et al., compare the optical performances of low order, zero order and total internal reflection (TIR) based retarders. The conclusion is that, even though TIR retarders are more sensitive to the beam alignment and aperture than the low order and zero order plates, they seem to be the optimum choice to be integrated into wide range spectroscopic systems because of their enhanced achromatism.

Concerning achromatic retarders, an article of Oxley {Phil. Mag., (1911)} has been considered because it gives some insight on the manufacture of two types of TIR based quarter wave retarders that do not deviate the beam when they are rotated. One of them is a V-shaped retarder made of two Fresnel rhombs, called bi-prism. The bi-prism geometry has become popular because of the easiness of construction and high achromaticity.

A patent of Thomson et al. {U.S. Pat. No 5,706,212}, describes an infrared ellipsometer/polarimeter system using pseudo-achromatic retarders. Each one of said retarders consists of a bi-prism cut to a given angle in order to create a total retardation of $\frac{3}{4}\lambda$. In a preferred embodiment, the ellipsometer has two retarders located respectivelly before and after the sample. During current operation of the ellipsometer/polarimeter, each retarder is rotated to a minimum of nine 9 azimuthal angle settings leading to at least eighty one 81 different raw data acquisitions. These acquisitions are then decomposed in terms of a double discrete Fourier series. From the coefficients of the said Fourier series, it is possible to calculate the characteristic Mueller matrix of the sample and of the optical components of the ellipsometer/polarimeter.

SUMMARY OF THE INVENTION

One aim of the present invention consists to provide an ellipsometer/polarimeter system allowing simpler data analysis with less parameters for the calculation of the Mueller matrix, and without a signal processing based on a series expansion, such as a Fourier series. As a result, the time needed for measurements and data treatment are then reduced.

Another aim of the invention is to provide a ellipsometer/polarimeter system comprising substantially achromatic retarders with optimized retardation to guarantee a uniform quality of the measurements for all the wavelengths in the light beam, and an optimization of the system performance by minimizing the propagation of noise and errors in the calculation of the Mueller matrix.

To this end, the invention concerns a broadband ellipsometer/polarimeter system for analysing a sample comprising:
- an illumination source emitting a polychromatic light beam,
- a polarisation state generator (PSG) including a fixed linear polarizer and a substantially achromatic retarder mounted on a rotating holder, said light beam passing through said PSG,
- a sample holder, on which the sample can be mounted, the light beam being focused on the sample,
- a polarisation state analyser (PSA) including a fixed linear polarizer and a substantially achromatic retarder mounted on a rotating holder, the beam going through said PSA, after being transmitted, reflected or scattered by the sample.
- a primary detection system measuring the intensity of the light beam transmitted through said PSA at each wavelength,
- optics to collimate the beam into the PSG and into the PSA and to focus the beam into the sample surface.

According to the invention:
- said linear polarizer and said substantially achromatic retarder in the PSA are identical to the linear polarizer and the substantially achromatic retarder of the PSG and inverted according to the sense of propagation of the light. Here, "identical" means either "the same elements", or "equivalent elements with the same optical properties",
- said rotating holders run in a stepper mode allowing a set of only four selected orientation angles for the retarders, said set of four selected orientation angles being optimized in order to maintain the condition numbers of the modulation and analysis matrices associated respectively with the PSG and the PSA over 0.2.

According to various embodiments, the present invention also concerns the characteristics below, considered individually or in all their technical possible combinations:
- the substantially achromatic retarder of the PSG is a total internal reflection based retarder providing a phase-shift of either $\{132°\pm30°+n360°\}$ or $\{227°\pm30°+n360°\}$, for all the wavelength light beam, with "n" being any integer,
- the substantially achromatic retarder of the PSA is a total internal reflection based retarder providing a phase-shift of either $\{132°\pm30°+n360°\}$ or $\{227°\pm30°+n360°\}$, for all the wavelengths of the light beam, with "n" being any integer,
- the substantially achromatic retarder of the PSG is placed at a set of four selected orientation angles $\theta_1$, $\theta_2$, $\theta_3$ and $\theta_4$, said $\theta_1$ being either $\{38\pm20°+n360°\}$ or $\{218\pm20°+n360°\}$, said $\theta_2$, being either $\{75\pm20°+n360°\}$ or $\{255\pm20°+n360°\}$, said $\theta_3$ being either $\{104\pm20°+n360°\}$ or $\{284\pm20°+n360°\}$, and said $\theta_4$ being $\{142\pm20°+n360°\}$ or $\{322\pm20°+n360°\}$, with "n" being any integer,
- the substantially achromatic retarder of the PSA is placed at a set of four selected orientation angles $\theta_1$, $\theta_2$, $\theta_3$ and $\theta_4$, said $\theta_1$ being either $\{38\pm20°+n360°\}$ or $\{218\pm20°+n360°\}$, said $\theta_2$, being either $\{75\pm20°+n360°\}$ or $\{255\pm20°+n360°\}$, said $\theta_3$ being either $\{104\pm20°+n360°\}$ or $\{284\pm20°+n360°\}$, and said $\theta_4$ being $\{142\pm20°+n360°\}$ or $\{322\pm20°+n360°\}$, with "n" being any integer,
- the substantially achromatic retarder of the PSG and the PSA comprises at least two prisms, each substantially achromatic retarder causing at least four internal reflections to the light beam entering on it and said beam is not deviated,
- the substantially achromatic retarder of the PSG is a "V" shaped bi-prism, consisting of two rhombs having an identical shape, optically assembled by one of their sides,
- the substantially achromatic retarder of the PSA is a "V" shaped bi-prism, consisting of two rhombs having an identical shape, optically assembled by one of their sides,
- the substantially achromatic retarder of the PSG comprises three triangular prisms from which, at least two have an identical shape,
- the substantially achromatic retarder of the PSA comprises three triangular prisms from which, at least two have an identical shape,
- the substantially achromatic retarder of the PSG comprises three prisms, two prisms of said three prisms are triangular and one prism is trapezoidal,
- the substantially achromatic retarder of the PSA comprises three prisms, two prisms of said three prisms are triangular and one prism is trapezoidal,
- the substantially achromatic retarder of the PSG comprises four trapezoidal prisms having an identical shape,
- the substantially achromatic retarder of the PSA comprises four trapezoidal prisms having an identical shape,
- each prism is made of a material with an index of refraction greater than that of the surrounding media,
- the entrance and exit faces of the retarders comprise an antireflection treatment (coating) to minimise light insertion losses,
- the faces of the prisms wherein total internal reflection takes place, are uncoated,
- the prisms of the substantially achromatic retarders are made of a material presenting a low index of refraction like the $BaF_2$,
- the primary detection system measures simultaneously the intensity of all the wavelengths of the light beam transmitted through said PSA,
- the primary detection system measures simultaneously and separately the intensity of each wavelength of the light beam transmitted through said PSA,
- the system includes a holder for reference samples, said holder is placed between the PSG and the sample holder, said holder introduce a set of reference samples in the beam path during calibration, and remove them during measurement process,
- the system includes a holder for reference samples, said holder is placed between the sample holder and the PSA, said holder introduce a set of reference samples in the beam path during calibration, and remove them during measurement process, said system includes a secondary detection system to monitor the power given by the illumination source including a beam-splitter located between the illumination source and the PSG and a secondary detector, said system operates in a spectral range from 4 to 20 microns, said system operates in a FUV-NIR spectral range from 140 nm to 2000 nm.

BRIEF DESCRIPTION OF THE DRAWINGS

To facilitate the description of the invention, the following drawings are provided in which.

DESCRIPTION OF THE PREFERRED EMBODIMENT

Figure 1:
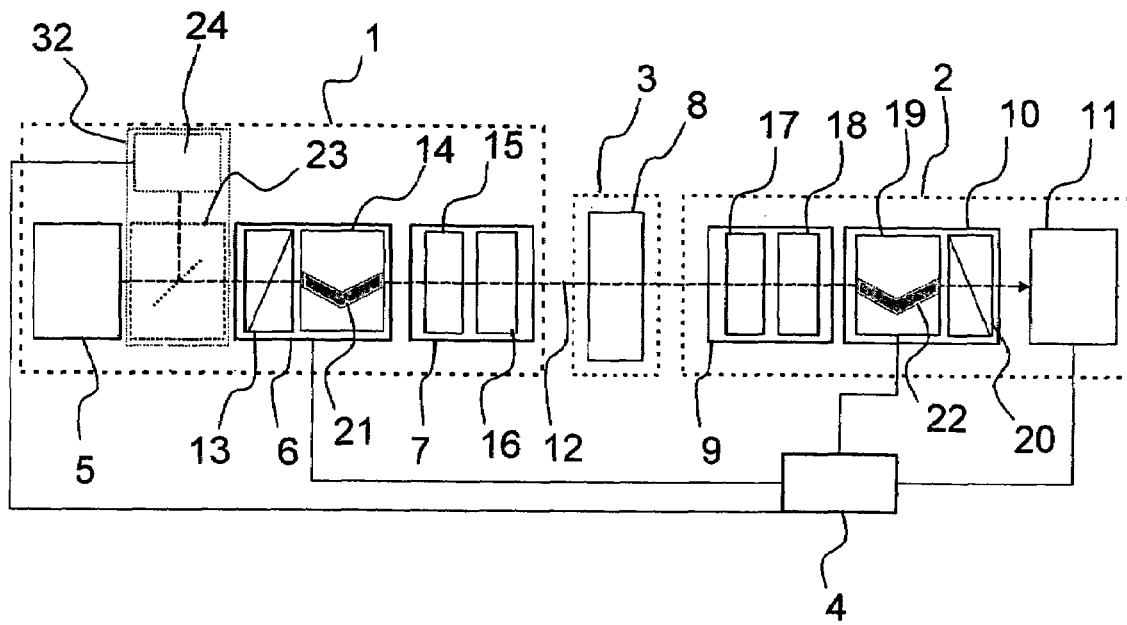
FIG. 1 is a functional block diagram of the ellipsometer/polarimeter system in transmission configuration, according to a particular embodiment of the invention.
Figure 2:
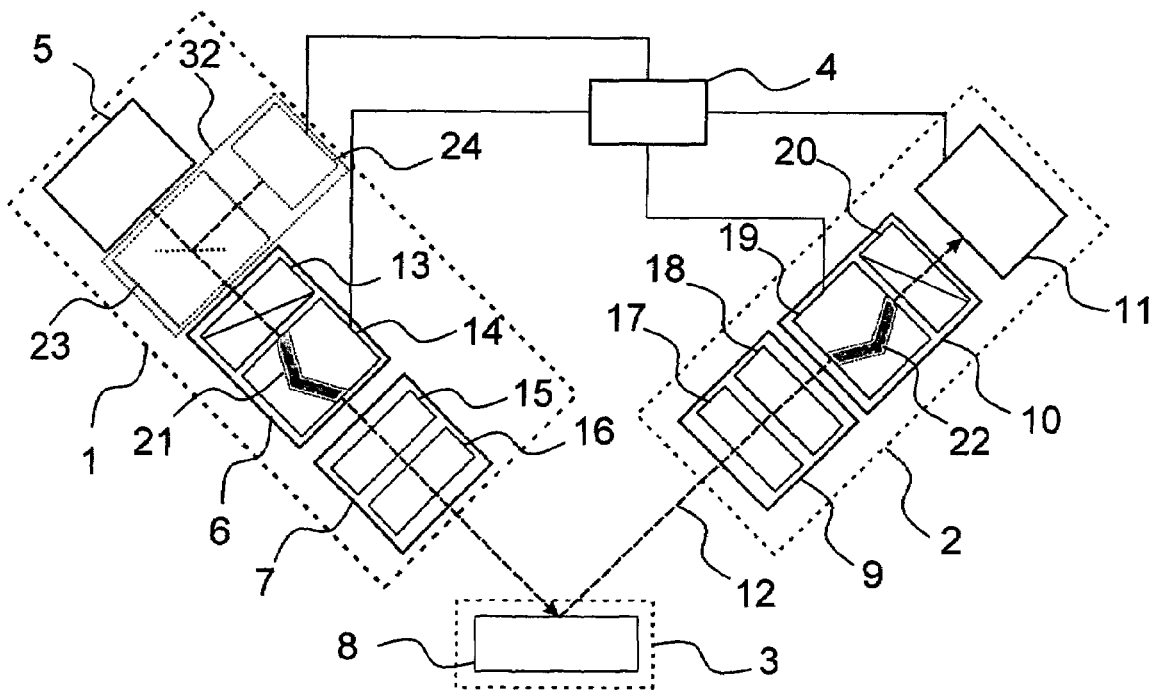
FIG. 2 is a functional block diagram of the ellipsometer/polarimeter system in reflection configuration, according to a particular embodiment of the invention.

FIG. 1 and FIG. 2 represent a functional block diagram of the disclosed ellipsometer/polarimeter system mounted respectively in transmission configuration and in reflection configuration according to two particular embodiments of the invention.

Said systems include an entrance arm 1, a sample holder system 3 to fix the studied sample 8, and an exit arm 2. The entry arm 1 includes an illumination source 5, a polarization state generator or PSG 6 and a holder for reference samples 7.

The PSG 6 includes a linear polarizer 13 and a substantially achromatic retarder 21. The retarder of the PSG 21 is mounted on a rotating holder 14 that allows it to be placed at different orientations.

The exit arm 2 includes a second holder for reference samples 9, a polarisation state analyser or, PSA 10, and a primary detection system 11 measuring the intensity of the light beam transmitted through said PSA (10) at each wavelength.

The PSA 10 has the same elements that the PSG 6, a linear polarizer 20 and a substantially achromatic retarder 22, but located in reverse order (inverted according to the sense of propagation of the light).

The retarder of the PSA 22 is mounted on a rotating holder 19 allowing it to be set at different orientations. The holders for the reference samples 7 and 9, introduce a set of specific samples 15, 16, 17 and 18 in the beam path during calibration, and remove them during measurement process. The optical path starts with the beam 12 emitted by the illumination source 5. Said light beam 12 passes through the PSG 6 and is focused on the sample 8 on the sample holder system 3.

After reflection on the sample surface, the beam goes through the analysis section 2, containing the PSA 10, and is finally focused into the sensitive area of the primary detection system 11.

The optical set-up is completed with the appropriate optics to collimate the beam into the PSG 6 and into the PSA 10, and to focus the beam into the sample 8 surface and the sensitive area of the primary detection system 11.

In one embodiment of the invention, the primary detection system 11 measures simultaneously the intensity of all the wavelengths of the light beam transmitted through the PSA 10.

In another embodiment of the invention, the primary detection system 11 measures simultaneously and separately the intensity of each wavelength of the light beam transmitted through the PSA 10

The primary detection system 11 is linked to a computer or a data acquisition and processing system 4. The computer 4, or an equivalent tool, allows to monitor the detection systems 11, 32 signals, to store raw data and to perform pertinent mathematical treatment of the raw data to obtain Mueller matrices, ellipsometric $\Psi$ and $\Delta$ angles, as well as other derived data. The computer 4 also controls the position of the rotating holders 14, 19 and the holders for the reference samples 7, 9.

The system can also include, as an option, a secondary detection system 32 made of a beam-splitter 23 and a secondary detector 24. The beam-splitter 23 is located between the illumination source 5 and the PSG 6 and it sends a small portion of the beam power towards the secondary detector 24. The signal measured by the secondary detector 24 can be used, among others, as a reference to normalize the signals measured by the primary detection system 11. Data normalization prevents errors due to power fluctuations of the beam 12 emitted by the source 5.

The use of substantially achromatic optical elements (polarizers 13, 20 and retarders 21, 22) guarantees a uniform quality of the measurements through the studied spectral range.

The advantage of rotating the retarders 21, 22 instead of the polarizers 13, 20 is to prevent the influence of the original polarization of the beam 12.

The PSG 6 generates four polarization states by placing sequentially the retarder of the PSG 21 at four selected orientations respect to the transmission axis of the PSG polarizer 13.

The rotation motion of the retarder 21 is not continuous; the rotating holder 14, runs in a stepper mode, thus making a key difference with respect to other reported rotating compensator ellipsometers/polarimeters.

Indeed, the small number of states produced by the PSG 6, (four instead of nine), in comparison with a previously described apparatus of the document U.S. Pat. No. 5,706,212, makes its operation faster and simpler.

Like in the PSG 6, the retarder of the PSA 22 is mounted in a rotating holder 19 that allows it to be oriented at four different angles with respect to the transmission axis of the polarizer of the PSA 20.

The four selected orientation angles for the two retarders 21 and 22 are optimized in order to maintain the condition numbers of the modulation and the analysis matrices associated respectively with the PSG 6 and the PSA 10 over 0.2.

Optionaly, the four selected orientation angles for the two retarders 21 and 22 are approximately identical.

After reflection or transmission by the sample 8, each one of the polarization states that had been originally generated by the PSG 6, is successively analyzed four times by the PSA 10, giving as a result 16 independent intensity measurements (raw data) necessary for the determination of the Mueller matrix.

The four polarization states generated in the PSG 6, as well of the optical configurations of the PSA 10, are not obvious or intuitive; they have been selected according to an objective criterion (condition numbers) that allows the minimization of the propagation of errors from the measurement to the computed Mueller matrix.

In the following, the mathematical description of the PSG 6 used to define the criterion for instrument optimization is reviewed. Because the PSA 10 is identical to the PSG 6, the physical principles, the mathematical description and the technological parameters giving rise to the optimization of the PSG 6 are also applicable to the PSA 10. It is common to use a 4×4 matrix, W, called modulation matrix, to represent the PSG 6 and an analysis matrix, A, to represent the PSA 10. The columns of the W matrix correspond to the four Stokes vectors generated by the PSG 6. Reciprocally, for each state generated by the PSG 6, the corresponding polarization state of the emerging light is projected over four optical configurations generated by the PSA 10. The four dimensional signal vector D, eventually delivered by the PSA 10, is related to each Stokes vector $S_{out}$ generated by the PSG by a linear relation $D=AS_{out}$.

The result of a complete polarimetric measurement, consists of sixteen independent raw intensity measurements that can be expressed by a matrix B=AMW, where A and W are respectively the analysis and modulation matrices defined above, and M the Mueller matrix of the sample. If A and W are known, then M can be extracted from the raw data B as $M=A^{-1}BW^{-1}$. The determination of A and W is called calibration of the polarimeter.

Obviously, the instrument must be designed in such a way that A and W are non singular. Moreover, in order to minimize the error propagation from the raw measurement B to the final result M, the analysis and modulation matrices A and W must be "as close as possible" to unitary matrices.

The best criterion in this respect is to optimize their condition numbers c(A) and c(W), which are the ratios of the smallest over the largest of their singular values, see for example W. H. Press et al. {Numerical Recipes in PASCAL, p 53}, who actually define the condition number as the reciprocal of that defined here.

In order to find the values of the azimuths and the retardation of the retarder 21 that optimize c(W), a convenient approach is to simulate the optical behaviour of PSG 6 treating the polarizer 13 and the retarder 21 as ideal. The ideal Mueller matrix for the polarizer 13 is:

$$P = \tau_P \begin{pmatrix} 1 & 1 & 0 & 0 \\ 1 & 1 & 0 & 0 \\ 0 & 0 & 0 & 0 \\ 0 & 0 & 0 & 0 \end{pmatrix} \qquad (1)$$

with $\tau_P$ being the polarizer 13 transmittance. The matrix of an ideal retarder 21 with transmittance $\tau_R$, a retardation δ, set at an azimuth "θ" is:

$$C(\theta, \delta) = \tau_R \begin{pmatrix} 1 & 0 & 0 & 0 \\ 0 & \cos^2(2\theta) + \cos(\delta)\sin^2(2\theta) & \sin^2\left(\frac{\delta}{2}\right)\sin(4\theta) & -\sin(\delta)\sin(2\theta) \\ 0 & \sin^2\left(\frac{\delta}{2}\right)\sin(4\theta) & \cos^2(2\theta) + \cos(\delta)\sin^2(2\theta) & \sin(\delta)\cos(2\theta) \\ 0 & \sin(\delta)\sin(2\theta) & -\sin(\delta)\cos(2\theta) & \cos(\delta) \end{pmatrix} \qquad (2)$$

Assuming that the light entering the PSG 6 is completely depolarized, the Stokes vector of the vector leaving the PSG 6 is given by the following expression:

$$S_{out}(\theta, \delta) = C(\theta, \delta) \cdot P \cdot \begin{pmatrix} 1 \\ 0 \\ 0 \\ 0 \end{pmatrix} \qquad (3)$$

Finally, a complete W matrix can be built by taking the four Stokes vectors obtained for the azimuths $\theta_i$, i=1 to 4, and for a common value for the retardation "δ":

$$W(\theta_1, \theta_2, \theta_3, \theta_4, \delta) = \qquad (4)$$

$$\begin{pmatrix} S_{out}(\theta_1,\delta)_1 & S_{out}(\theta_2,\delta)_1 & S_{out}(\theta_3,\delta)_1 & S_{out}(\theta_4,\delta)_1 \\ S_{out}(\theta_1,\delta)_2 & S_{out}(\theta_2,\delta)_2 & S_{out}(\theta_3,\delta)_2 & S_{out}(\theta_4,\delta)_2 \\ S_{out}(\theta_1,\delta)_3 & S_{out}(\theta_2,\delta)_3 & S_{out}(\theta_3,\delta)_3 & S_{out}(\theta_4,\delta)_3 \\ S_{out}(\theta_1,\delta)_4 & S_{out}(\theta_2,\delta)_4 & S_{out}(\theta_3,\delta)_4 & S_{out}(\theta_4,\delta)_4 \end{pmatrix}$$

Sub-indexes 1 to 4 placed next to the parentheses refer to the components of each one of Stokes vectors generated by the PSG 6. Under the above representation, the condition number of the matrix W can be understood as a function of five parameters, the retardation δ and the four azimuth angles of the retarder 21. In an article, Tyo et al. {Appl. Opt., (2002)} has shown that for a PSG or a PSA made essentially with polarizers and retarders, the theoretical value of the condition number can vary between "0" and "$3^{-1/2}$". Accordingly, the values of the five parameters, retardation and azimuths, used to design the PSG 6, must be those that optimize the value of the condition number.

Finding the value of the parameters that maximize the condition number is a numerical problem that can be solved by means of a standard optimization routine such as the Simplex or the Levenberg-Marquardt {Numerical Recipes in PASCAL, p. 326}. As a result, two optimal values for the retardation and two values for each one of the azymuts $\theta_1$, $\theta_2$, $\theta_3$ and $\theta_4$ can be found. Once the optimal values are determined, the sensitivity of the PSG 6 or the PSA 10 to fluctuations of retardation and orientation angles can be estimated using the condition number, again, as a criterion. In fact, even though the condition number can be theoretically very small, it is commonly accepted that a minimum value of 0.2 is needed to obtain measurements with acceptable quality. Accordingly, the tolerances of the retardation, and the four azimuths of the retarder around their respective optimum value, are specified in order to maintain the condition number over 0.2.

The values for the retardation are:

$\delta_1 = 132° + n360°$ and $\delta_2 = 227° + n360°$, with "n" being any integer.

Figure 3:
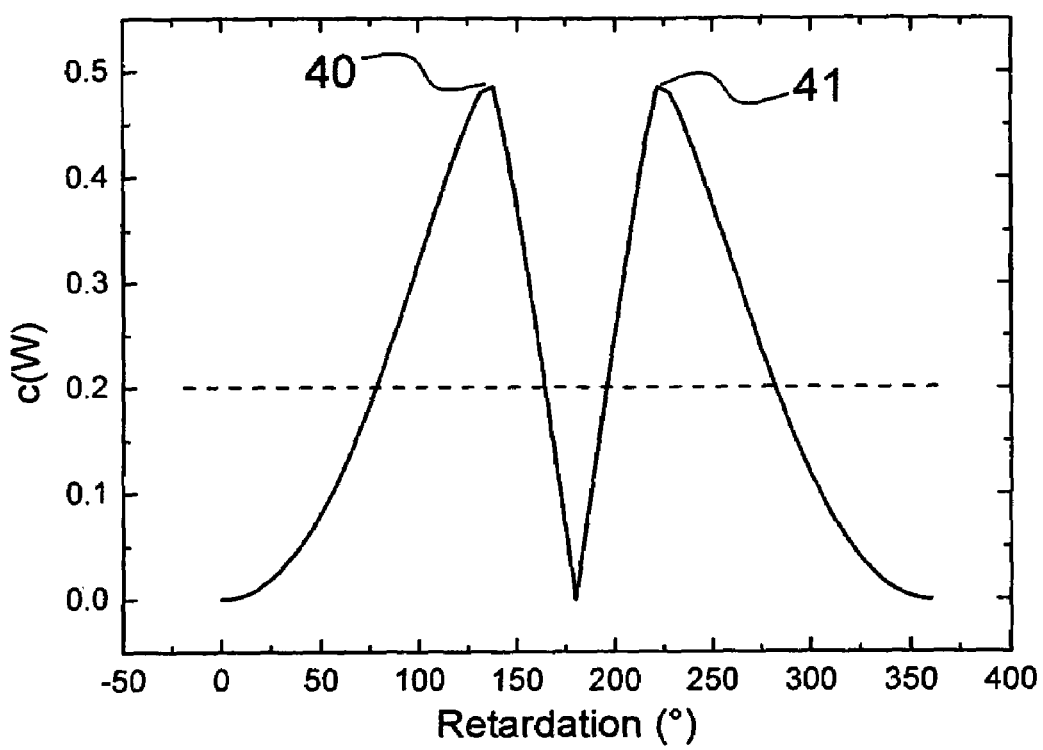
FIG. 3 displays the condition number of the PSG as a function of the phase-shift of a retarder for a given set of four optimal azimuth orientations.

FIG. 3 shows the values of the condition number calculated as function of the retardation for one set of optimal values of the azimuths.

The two maxima 40 and 41, correspond respectively to the values for the retardation $\delta_1$ (132°) and $\delta_2$ (227°).

From this figure, and in accordance with the former definition, it can be seen that the tolerance for the retardation can be evaluated to about ±30°.

The optimal values for the azimuths are are:

$\theta_1 = 38° + n360°$ or $218° + n360°$ $\theta_2 = 74° + n360°$ or $254° + n360°$ $\theta_3 = 106° + n360°$ or $286° + n360°$ $\theta_4 = 142° + n360°$ or $322° + n360°$ with "n" being any integer.

FIGS. 4 to 7 show the values of the condition number calculated as a function of the azimuths $\theta_1$, $\theta_2$, $\theta_3$, and $\theta_4$ respectively. From those figures, and in accordance with the former definition, it can be seen that the tolerance for the angles $\theta_1$, $\theta_2$, $\theta_3$, and $\theta_4$ can be evaluated to about ±20°.

Figure 4:
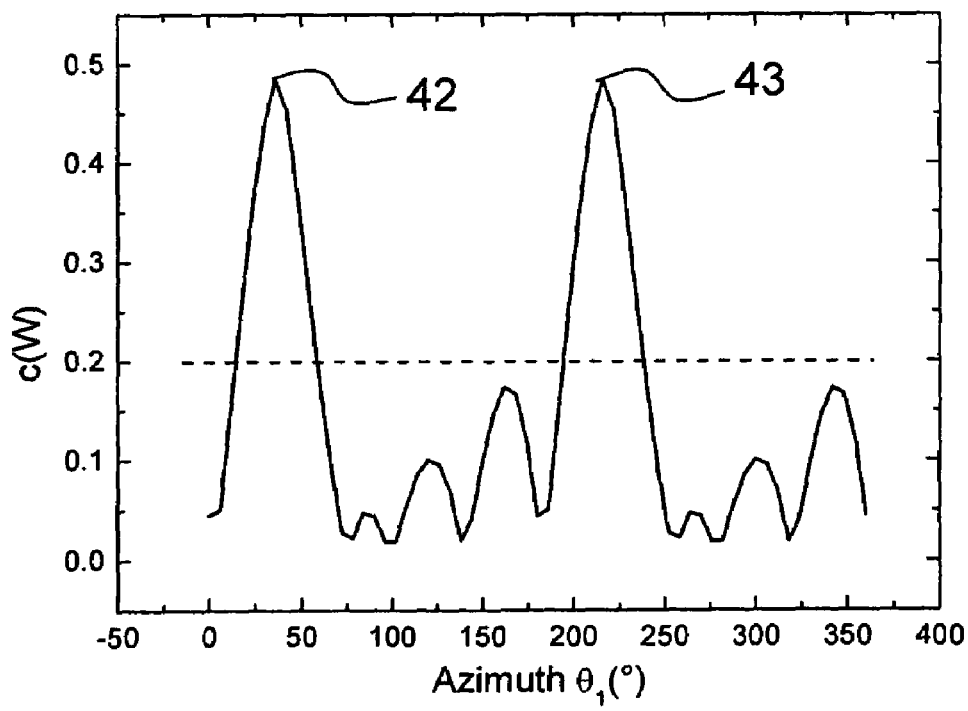
FIG. 4 shows the values of the condition number calculated as a function of the retarder azimuth $\theta_1$, with the other three azimuths and the retardation kept constant to their optimum value.

In FIG. 4, the two maxima 42 and 43 correspond respectively to the two possible values of azimuths $\theta_1$ (38°+n360° and 218°+n360°) with n being any integer. These values have been calculated assuming the optimum values for the retardation and the azimuths $\theta_2$, $\theta_3$, and $\theta_4$.

Figure 5:
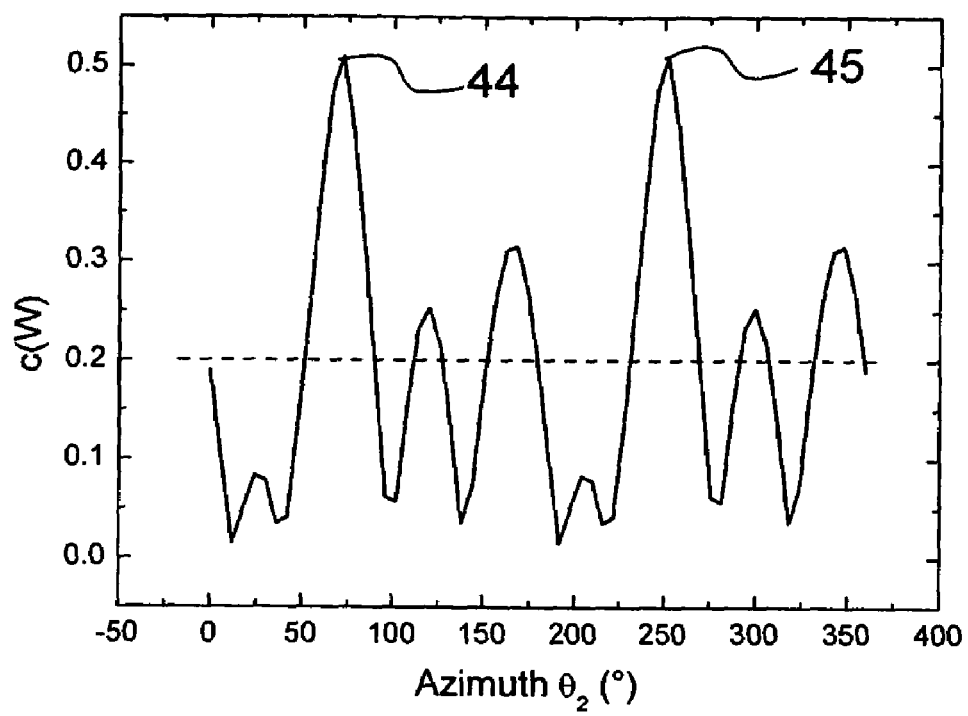
FIG. 5 shows the values of the condition number calculated as a function of the retarder azimuth $\theta_2$ with the other three azimuths and the retardation kept constant to their optimum value.

In FIG. 5, the two maxima 44 and 45 correspond respectively to the two possible values of azimuths $\theta_2$ (74°+n360° and 254°+n360°) with n being any integer. These values have been calculated assuming the optimum values for the retardation and the azimuths $\theta_1$, $\theta_3$, and $\theta_4$.

Figure 6:
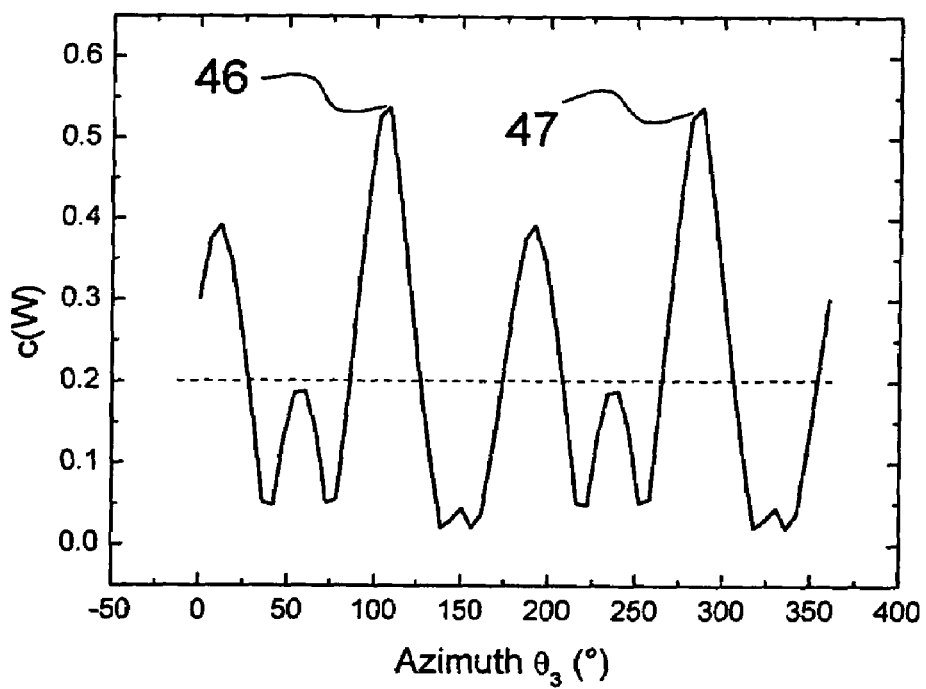
FIG. 6 shows the values of the condition number calculated as a function of the retarder azimuth $\theta_3$ with the other three azimuths and the retardation kept constant to their optimum value.

In FIG. 6, the two maxima 46 and 47 correspond respectively to the two possible values of azimuths $\theta_3$ (106°+n360° and 286°+n360°) with n being any integer. These values have been calculated assuming the optimum values for the retardation and the azimuths $\theta_1$, $\theta_2$, and $\theta_4$.

Figure 7:
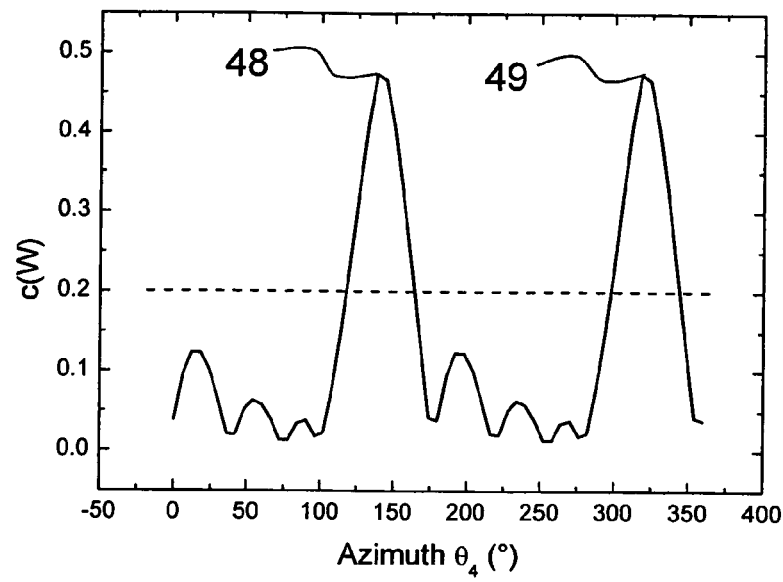
FIG. 7 shows the values of the condition number calculated as a function of the retarder azimuth $\theta_4$ with the other three azimuths and the retardation kept constant to their optimum value.

In FIG. 7, the two maxima 48 and 49 correspond respectively to the two possible values of azimuths $\theta_4$ (142°+n360° and 322°+n360°) with n being any integer These values have been calculated assuming the optimum values for the retardation and the azimuths $\theta_1$, $\theta_2$, and $\theta_3$.

In view of the constraints imposed by the condition number of the PSG 6 and the PSA 10, a broadband ellipsometer/polarimeter intended to perform optimally over all the spectral range, must include a retarder 21 as much achromatic as possible providing a retardation close to 132° for all the wavelengths. To achieve this objective, three TIR based achromatic retarders are proposed.

Figure 8:
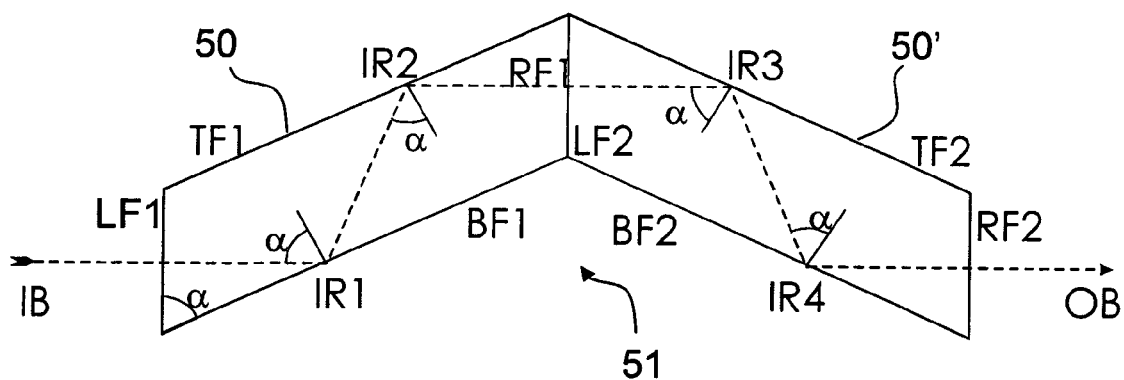
FIG. 8 displays a substantially achromatic retarder consisting of a bi-prism made of two identical Fresnel rhombs disposed symmetrically and optically assembled giving to the retarder a "V" shape.

The first retarder shown in FIG. 8, consists of a bi-prism 51 made of two identical Fresnel rhombs disposed symmetrically and joined by optical contact, giving to the retarder a "V" shape. We mean with "identical" that the Fresnel rhombs present the same form. The two identical Fresnel rhombs are not necessarily made of the same material.

In more detail, the bi-prism 51 includes a first 50 and a second 50' rhombs which, as viewed in side elevation, have each a top TF1/TF2, and bottom BF1/BF2 faces oriented at an angle (90°−α) respect to the horizontal.

Said first 50 and second 50' rhombs have right RF1/RF2 and left LF1/LF2 faces parallel respect to each other and oriented vertically. Said first 50 and second 50' rhombs are made of a material with an index of refraction greater than the surrounding medium (usually air, but not mandatory). A rightmost vertically oriented face RF1 of the first rhomb 50 is in contact with the leftmost face LF2 of the second rhomb 50'. The input beam IB penetrates into the first rhomb 50 through its leftmost side LF1 at normal incidence, then reaches a locus in the bottom face BF1 at an angle of incidence α, and undergoes a first total internal reflection IR1, then, said beam reaches the top face TF1 with an angle of incidence α, and undergoes a second total internal reflection IR2. After said second internal reflection IR2, the beam reaches at normal incidence the interface between the first 50 and second 50' rhombs defined by the leftmost face LF1 of the first rhomb 50 and the rightmost face RF2 of the second rhomb 50'. Once the beam is inside the second rhomb 50', it reaches a locus in the top face TF2 with an angle of incidence α, where it undergoes a third total internal reflection IR3. Finally, said beam reaches the bottom face BF2 with an angle of incidence α, and undergoes a fourth total internal reflection IR4. After said fourth internal reflection IR4 the beam reaches at normal incidence the rightmost face RF2 and it exits the bi-prism 51. As a result, the output beam OB is not deviated respect to the input beam IB even in the case of rotation of the bi-prism 51.

This configuration induces four total internal reflections and prevents the beam emerging from the bi-prism 51 to be deviated from its original direction. The total amount of retardation created by a bi-prism in contact with the air is the sum of retardations caused by each one of the internal reflections. When the bi-prism 51 is in contact with the air, the most general case, the retardation introduced by each total internal reflection can be expressed as:

$$\delta_{oneTIR} = 2\tan^{-1}\left(\frac{\cos\phi(n^2\sin^2\phi - 1)^{1/2}}{n\sin^2\phi}\right) \quad (5)$$

where φ is the angle of incidence for the internal reflection and "n" is the index of the material where the TIR takes place. The normal incidence of the beam at the interface between the rhombs 50, 50', prevents it to be deviated, even if the rhombs are not built of the same material. This is an advantage that allows the combination of different materials in order to enhance the achromaticity of the bi-prism. The entrance and exit faces of the bi-prism 51 are perpendicular to the propagation direction of the beam in order to make insertion losses independent of the polarization. From geometrical considerations, it is easy to show that the angle of incidence φ in the expression 5 corresponds to the angle α mentioned previosly, that determines the shape of the bi-oprism. According to expression 5 and for a given value of the total retardation, high values of "n" allow small angles of incidence, thus leading to short and compact retarders.

However, the use of high index materials to build the bi-prism 51 can create some optical drawbacks. First, the high contrast of index between the surrounding medium and the prism can induce important insertion losses if the entrance (exit) faces do not have an adequate antireflection coating. Secondly, in the absence of an antireflection coating, the transmission faces, which are parallel to each other, can generate multiple-internal reflected secondary beams inside the prism. Those multiple-reflected beams have performed multiple travels in the interior of the prisms, thus cumulating a phase-shift different from that of the principal beam. When the contrast of index is high, the relative intensity of the secondary beams cannot be neglected, and their superposition with the principal beam causes non-idealities, such as depolarization, in the behaviour of the retarder that can not be predicted by a simple addition of the retardations given by expression 5.

Consequently, with uncoated high index materials, the performance, i.e. the condition number, of the PSG 6 can be considerably decreased. If there are no constraints on the size of the bi-prisms 51, one possible solution to those drawbacks is to build them with low index, "n", materials such as $BaF_2$ (1.51 @ 265 nm, 1.39 @ 10 micron) among others because insertion losses and intensity of multiple-reflected beams are minimized. Materials like $BaF_2$ have also the advantage of being transparent over a wide spectral range from the ultraviolet to the infrared, so they are the ideal candidates to be used in the construction of bi-prisms. $BaF_2$ is mentioned here for illustrative purposes only and should not be used to unduly limit the scope of the invention.

Figure 9:
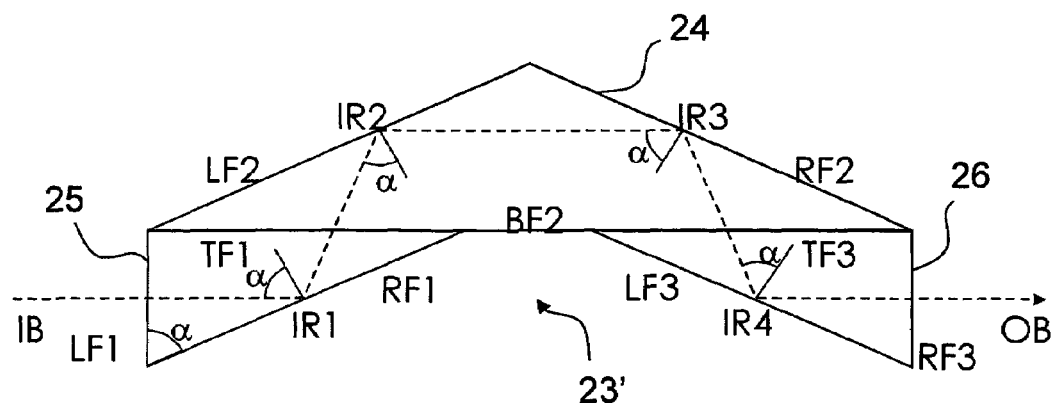
FIG. 9 displays a particular embodiment of a substantially achromatic retarder made of a set of three triangular prisms optically assembled.

FIG. 9 is a schematic frontal view of a second substantially achromatic retarder 23' according to another embodiment of the invention. Said second substantially achromatic retarder 23' is made of three triangular prisms 24, 25 and 26, joined by optical contact.

According to FIG. 9, the first prism 25 has a vertically oriented left face LF1 that makes an angle α with its right face RF1 and a right angle with its top face TF1. Similarly, the third prism 26 has a vertically oriented right face RF3 that makes an angle α with its left face LF3 and a right angle with its top face TF3. First 25 and third 26 triangular prisms are identical and are placed symmetrically with respect to each other.

The second prism has a horizontally oriented bottom face BF2 that is in contact with the first 25 and the third prism 26 through their respective top TF1 and TF3 faces. Said second prism 24 has a right face RF2 and a left face LF2 oriented at an angle of α with respect to the horizontal. The input beam IB reaches the second substantially achromatic retarder 23' through the left face LF1 of the first prism 25 at normal incidence. Once the said beam is in the first triangular prism 25, it reaches a locus in the right face RF1 with an angle of incidence α, and undergoes a first total internal reflection IR1. Then, said beam reaches the second triangular prism 24, through the interface defined by the BF2 and TF1, and reaches its left face LF2 with an angle of incidence α, and undergoes a second total internal reflection IR2. Then, said beam follows a trajectory parallel to the horizontal and reaches a locus in the right face RF2 with an angle of incidence α, before undergoing a third IR3 total internal reflection and to be sent to the third prism 26 through the interface defined by BF2 and TF3. On the third prism 26, said beam reaches its left face LF3 with an angle of incidence α, and undergoes a fourth total internal reflection IR4. Finally, said beam reaches the right face RF3 at normal incidence, and exits the system OB with a direction that is not deviated nor shifted respect to that of the initial input beam IB, even in the case of rotation of the substantially achromatic device 23'.

Again, like in the bi-prism 51, the transmitting faces are perpendicular to the beam direction in order to avoid polarization dependant insertion loses.

Because the beam is perpendicular to the input face of the prism, from geometrical considerations it is possible to show that the incidence angle in the first 25 and third 26 prisms is equal to α. Again, some simple geometrical considerations allow to show that if the direction of the beam must be preserved by the full device, the incidence angle of the two internal reflections on the second prism 24 must be equal to α. This implies that LF2 (resp. RF2) must be parallel to RF1 (resp. LF3).

The total retardation of the second substantially achromatic retarder 23' is the sum of the retardations suffered by the beam after the four total internal reflections, which are, in turn functions of the internal angle of incidence α, according to expression 5. As in the case of the bi-prism 51, retardation can be defined by the manufacture of the device if the refraction index is known.

Again, like in the case of the bi-prism 51 the expression 5 shows that for a given retardation, the use of materials of high index for the prisms results in small and compact devices, however, they can be affected by the same drawbacks caused by beam insertion losses and generation of multiple-reflected beams as in the case of the bi-prism 51. For this reason, low index materials, such as $BaF_2$ are preferred to build the second substantially achromatic retarder 23'.

Figure 10:
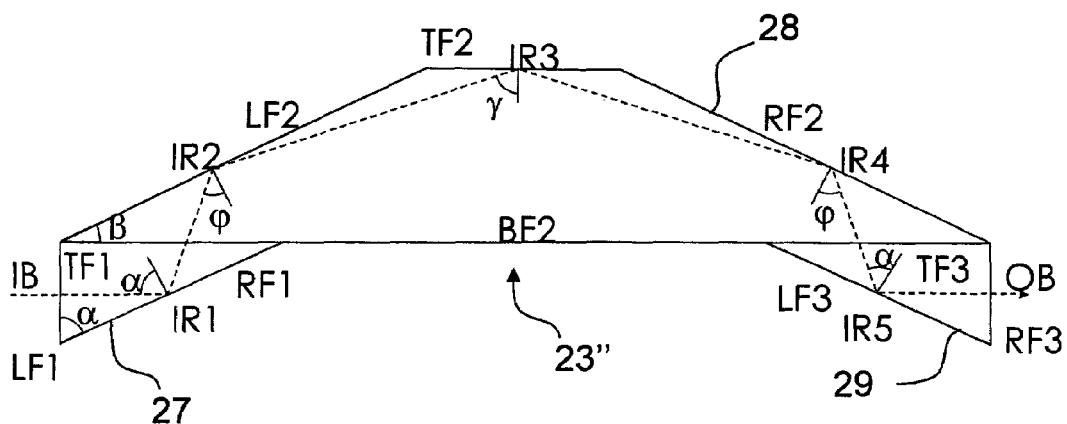
FIG. 10 displays another particular embodiment of a substantially achromatic retarder made of two triangular prisms and a third trapezoidal one optically assembled.

FIG. 10 is a schematic frontal view of a third substantially achromatic retarder 23". Said third substantially achromatic retarder 23" is made of two triangular prisms 27, 29 and a trapezoidal prism 28, joined by optical contact, according to another embodiment of the invention.

According to the schematic view shown in the FIG. 10, the first prism 27 has a vertical left face LF1, a horizontal top face TF1, and a tilted right face RF1. The left face LF1 defines an angle α with the right face RF1, and a right angle with the top face TF1. Similarly, the third prism 29 has a vertical right face RF3, a horizontal top face TF3, and a tilted left face LF3. The right face RF3 defines an angle $\alpha$ with the left face LF3, and a right angle with the top face TF3. First 27 and third 29 triangular prisms are identical and are located symmetrically with respect to each other.

We mean with "identical" that the first 27 and third 29 triangular prisms present the same form.

The second prism 28 has horizontally oriented top TF2 and bottom BF2 faces, and right RF2 and left faces LF2 oriented at an angle of $\beta$ respect to the horizontal. Said bottom face BF2 is in contact with the first 27 and the third prism 29 through their respective top (TF1 and TF3) faces. The input beam IB penetrates into the third substantially achromatic retarder 23" through the left face LF1 of the first prism 27 at normal incidence. Once said beam is in the first triangular prism 27, it reaches the right face RF1 with an angle of incidence $\alpha$, and undergoes a first total internal reflection IR1. Then, said beam reaches the second triangular prism 28 through the interface defined by the BF2 and TF1, and reaches its left face LF2 with an angle of incidence $\phi$, which is a function of $\alpha$ and $\beta$, and undergoes a second total internal reflection IR2. Then, said beam reaches the top face TF2 with an angle of incidence $\chi$ where it undergoes a third total internal reflection IR3. Said angle $\chi$ is a function of the angles $\alpha$ and $\beta$ and is different from angle $\phi$. Next, said beam reaches the right face RF2 with an angle of incidence $\phi$ and undergoes a fourth IR4 total internal reflection that sends it to the third prism 29 through the interface defined by BF2 and TF3. On the third prism 29, said beam reaches its left face LF3 with an angle of incidence $\alpha$ and undergoes a fifth total internal reflection IR5. Finally, said beam reaches the right face RF3 at normal incidence, and exits the system OB with a direction that is not deviated nor shifted respect to that of the initial input beam, even in the case of rotation of the substantially achromatic device.

The light beam undergoes five total internal reflections, and the outgoing beam propagates along the optical axis in the same direction as the incoming beam. Like in the previously described second substantially achromatic retarder 23', the transmitting faces are perpendicular to the beam direction in order to avoid insertion loses depending on the polarization.

Because the beam is perpendicular to the entrance (exit) face of the first 27 (third 29) prism, the incidence angle of the first and fifth internal reflections are equal to $\alpha$.

The trapezoidal prism 28 can be defined by an angle $\beta$ that can be different from $\alpha$. By convention, $\beta$ is defined as the angle between the face in contact with the triangular prisms 27, 29, and the face where takes place the second total internal reflection IR2. The angle of incidence of the second and fourth total internal reflection IR2, IR4 in the trapezoidal prism 28 is a function of the angles $\alpha$ and $\beta$. The angle of incidence of the third internal reflection IR3, $\chi$, is different from the angle of incidence of the second and the fourth total internal reflections IR2, IR4.

The total retardation of the third substantially achromatic retarder 23" is the sum over the retardations undergone by the beam after the five total internal reflections, which are in turn functions of each angle of incidence. An appropriate choice of $\alpha$, $\beta$ allows optimizing the value and the achromatism of the third substantially achromatic retarder 23".

Figure 11:
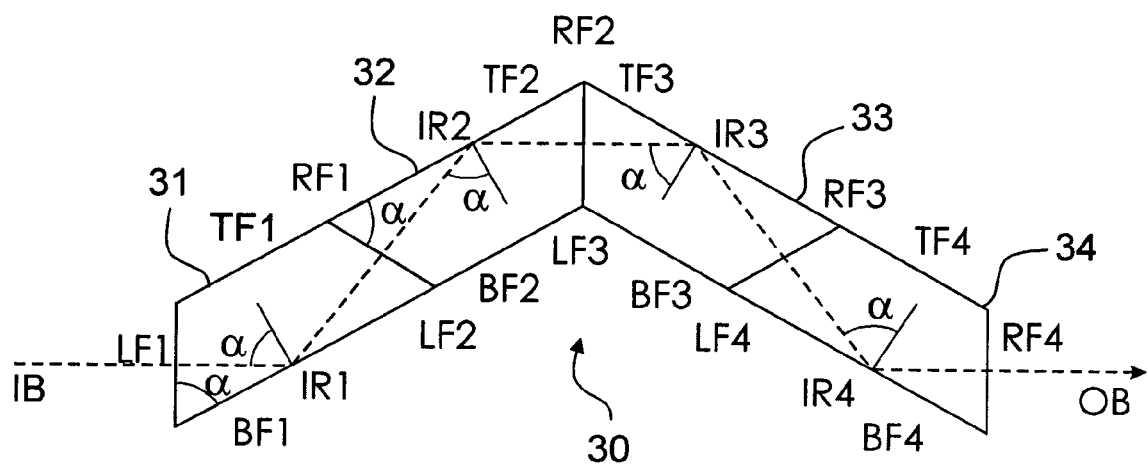
FIG. 11 displays another particular embodiment of a substantially achromatic retarder made of four identical trapezoidal prisms optically assembled.

FIG. 11 is a schematic frontal view of a fourth substantially achromatic retarder 30 according to another embodiment of the invention. Said second substantially achromatic retarder 30 is made of four identical trapezoidal prisms 31, 32, 33 and 34, joined by optical contact, and cut in order to the beam reaches their respective input and output interfaces at normal incidence.

We mean with "identical" that the four identical trapezoidal prisms 31, 32, 33 and 34 present the same form but not necessarily made of the same material.

This last condition imposes that all the prisms must be symmetric respect to the axis normal to the surface where the internal reflection takes place (see FIG. 11). Accordingly, the prisms 31 and, 34 have a leftmost face LF1, LF4, that makes an angle $\alpha$ with their respective bottom face BF1, and BF4. The prism 32 and 33 have a leftmost face LF2 and LF3 that makes an angle $\alpha$ with their respective top faces TF2 and TF3. In addition, because of symmetry, prisms 31 and 34 have a rightmost face RF1, and RF4 respectivelly, that makes an angle $\alpha$ with the corresponding bottom face BF1 and BF4, and prisms 32 and 33 have a rightmost face RF2 and RF3 that makes and angle $\alpha$ with the corresponding top faces TF2 and TF3. The right face RF1 of the first prism 31, is in contact with the left face LF2 of the second prism 32. The right face RF2 of the second prism 32, is in contact with the left face LF3 of the third prism 33. Finally, the right face RF3 of the third prism 33, is in contact with the left face LF4 of the fourth prism 34.

The input beam IB reaches the fourth substantially achromatic retarder 30 through the left face LF1 of the first prism 31 at normal incidence. Once said beam is in the first prism 31, it reaches a locus in its bottom face BF1 with an angle of incidence $\alpha$, and undergoes a first total internal reflection IR1. Then, said beam reaches the interface between the first 31 and the second prism 32 at normal incidence and arrives to the top face TF2 of the second prism 32, with an angle of incidence $\alpha$, and undergoes a second total internal reflection IR2.

Then, said beam follows a trajectory parallel to the horizontal, crosses the interface between the second 32 and the third 33 prisms at normal incidence, and reaches a locus in the top face TF3 of the third prism 33 with an angle of incidence $\alpha$, before undergoing a third IR3 total internal reflection and to be sent towards the fourth prism. After traversing the interface between the third 33 and the fourth 34 prism at normal incidence, said beam reaches its bottom face BF4 with an angle of incidence $\alpha$, and undergoes a fourth total internal reflection IR4. Finally, said beam reaches the right face RF4 at normal incidence, and exits the system OB with a direction that is not deviated nor shifted respect to that of the initial input beam IB, even in the case of rotation of the substantially achromatic device 30.

The transmitting faces LF1 and RF4 of the retarder 30 are perpendicular to the beam direction in order to avoid polarization dependent insertion losses. Because the beam reaches the three interfaces between prisms (RF1/LF2, RF2/LF3, RF3/LF4) at normal incidence, its trajectory is not deviated, even if different materials are used to build two adjoining prisms. This fact allows the combination of different materials to build the retarder 30 with enhanced achromaticity respect to an equivalent retarder built of only one material.

The total retardation of the fourth substantially achromatic retarder 30 is the sum of the retardations suffered by the beam after the four total internal reflections, which are, in turn, functions of the refraction index of each prism as well as the internal angle of incidence $\alpha$, according to expression 5.

Again, like in the case of the bi-prism 51, the expression 5 shows that the use of materials of high index for the prisms results in small and compact devices, however, they can be affected by the same drawbacks caused by beam insertion losses and generation of multiple-reflected beams as in the case of the bi-prism 51. For this reason, low index materials, such as $BaF_2$ are preferred to build the fourth substantially achromatic retarder 30.

Each prism 51, 23', 23" and 30 is made of a material with an index of refraction greater than that of the surrounding media.

The entrance and exit faces of the prisms 51, 23', 23" and 30 comprise an antireflection treatment (coating) to minimise light insertion losses.

The faces of the prisms 51, 23', 23" and 30 wherein total internal refection takes place, are uncoated.

The prisms 51, 23', 23" and 30 are made of a material presenting a low index of refraction like the $BaF_2$. $BaF_2$ is mentioned here for illustrative purposes only and should not be used to unduly limit the scope of the invention.

The disclosed broadband ellipsometer/polarimeter system is general and the spectral range is limited by the transmittance and other optical properties of the optical devices used to build it.

Accordingly, the disclosed system can lead to multiple implementations. The following are two examples of possible embodiments for the present invention. Those examples are presented here for illustration purposes only and should not be used to unduly limit the scope of the present invention.

The first example of a possible embodiment shown in FIGS. 1 and 2, previously described, includes a broadband ellipsometer/polarimeter system working from the far ultraviolet (around 140 nm) to the near infrared (2000 nm).

The illumination source 5 is an ultraviolet-visible source. The illumination source 5 provides a continuous beam 12 in a wide spectral range from the ultraviolet to the near infrared. Some examples of those kinds of sources 5 could be high pressure Hg—Xe discharge lamps or Deuterium-Halogen lamps The reratarder holders 14, 19 can be rotated, manually or automatically, following a predetermined sequence controlled by the computer 4.

In a preferred embodiment, the rotating holders 14, 19 are driven automatically by a motor running in stepper mode, connected to the computer 4 to ensure fast and repetitive movements.

Reference-sample-holders 7, 9 placed respectively after the PSG 6 and before the PSA 10, introduce reference samples 15, 16, 17, 18 in the beam path during calibration and remove them during current measurement process.

The computer 4 is intended to monitor the sequence of movements of the retarders 21, 22 either directly, or assisted by secondary specific controllers.

In addition, the computer 4 is also in charge of the acquisition of raw data from the detection unit and its subsequent treatment. The primary detector system 11 can be one or a combination of the types described in the following list:
- a single photodiode for a sequential detection of radiation resolved in wavelength coming from a spectrograph,
- a group of photodiodes to detect in parallel a group of selected wavelengths coming from a spectrograph,
- a single CCD array coupled to a spectrograph,
- a group of CCD arrays coupled to a spectrograph.

The best suited polarizers 13, 20 to work in the FUV-VIS range are those of either Rochon type or Glan type. Both retarders, 21 and 22 must be substantially achromatic, and provide a retardation close to 132°. In a preferred embodiment, retarder 21 must be either:
- a bi-prism 51 or,
- a retarder according to the description of the second substantially achromatic retarder 23', or
- a retarder according to the description of the third substantially achromatic retarder 23", or
- a retarder according to the description of the fourth substantially achromatic retarder 30', and the the retarder 22 must be:
- a bi-prism 51 or,
- a retarder according to the description of the second substantially achromatic retarder 23', or
- a retarder according to the description of the third substantially achromatic retarder 23", or
- a retarder according to the description of the fourth substantially achromatic retarder 30'.

According to the present invention, during the data acquisition, the retarder 21 in the PSG 6 is successively oriented at four defined angles $\theta_1$, $\theta_2$, $\theta_3$, and $\theta_4$, with $\theta_1$ being either 38° or 218°, $\theta_2$ being either 74° or 254°, $\theta_3$ being either 106° or 286° and $\theta_4$ being either 142° or 322°, to generate different polarization states that are sent to the sample. Each one of the four polarization states, after interacting with the sample, is projected against four optical configurations of the PSA 10, made by orienting retarder 22 at four different angles, $\theta_1$, $\theta_2$, $\theta_3$, and $\theta_4$, with $\theta_1$ being either 38° or 218°, $\theta_2$ being either 74° or 254°, $\theta_3$ being either 106° or 286° and $\theta_4$ being either 142° or 322°.

As a result, a set of sixteen $S_{i,j}$ measurements are obtained. The Mueller matrix of the sample 8 is obtained by multiplying the matrix S by the inverse of the matrices W and A corresponding to the PSG 6 and the PSA 10 respectively.

If the measured sample 8 corresponds to a non-depolarizing dichroic retarder, the ellipsometers angles $\Psi$ and $\Delta$ can be derived directly from the corresponding Mueller matrix because for this type of sample the following relations are always satisfied:

Upper diagonal block:

$$M_{11} = M_{22} = \tau$$

$$M_{12} = M_{21} = -\tau \cos(2\Psi) \qquad (6)$$

Lower diagonal block:

$$M_{33} = M_{44} = \tau \sin(2\Psi)\cos(\Delta)$$

$$M_{34} = -M_{43} = \tau \sin(2\Psi)\sin(\Delta) \qquad (7)$$

The remaining elements are null.

Alternatively, $\Psi$ and $\Delta$ can be evaluated directly from the eigenvalues of the Mueller matrix of a dichroic retarder, which can be written as:

$$\lambda_{R1} = 2\tau \sin^2(\Psi)$$

$$\lambda_{R2} = 2\tau \cos^2(\Psi) \qquad (8)$$

$$\lambda_{R3} = \tau \sin(2\Psi)\exp(i\Delta)$$

$$\lambda_{R4} = \tau \sin(2\Psi)\exp(-i\Delta) \qquad (9)$$

In order to minimize the errors due to intensity fluctuations of the illumination source 5, a reference measurement can be taken by splitting a part of the beam, and to measure it with the second detector 24.

Figure 12:
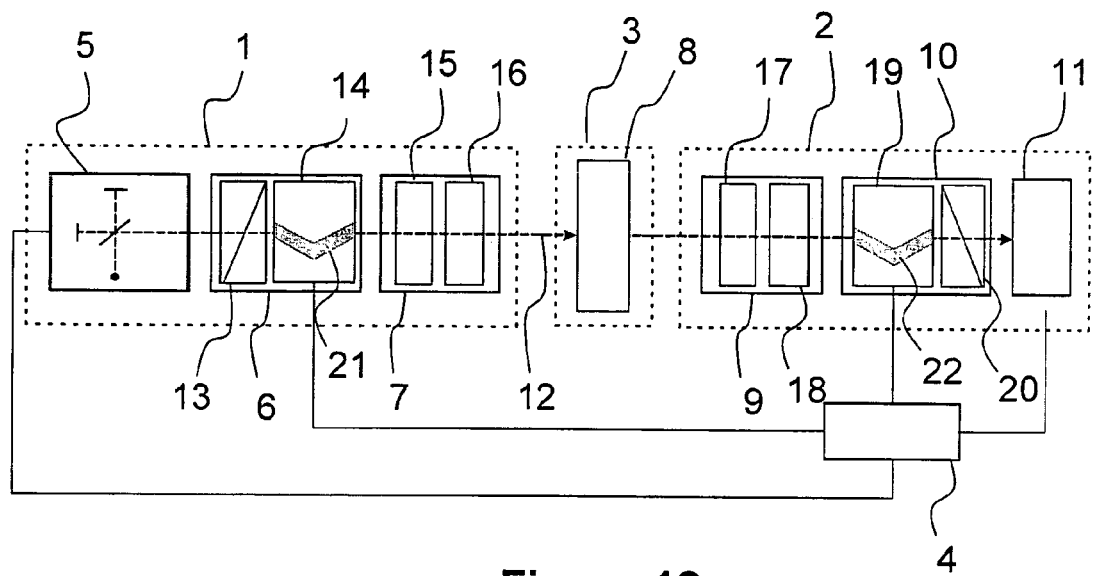
FIG. 12 is a schematic representation of a possible embodiment of the ellipsometer/polarimeter system optimized for the infrared, set in transmission.
Figure 13:
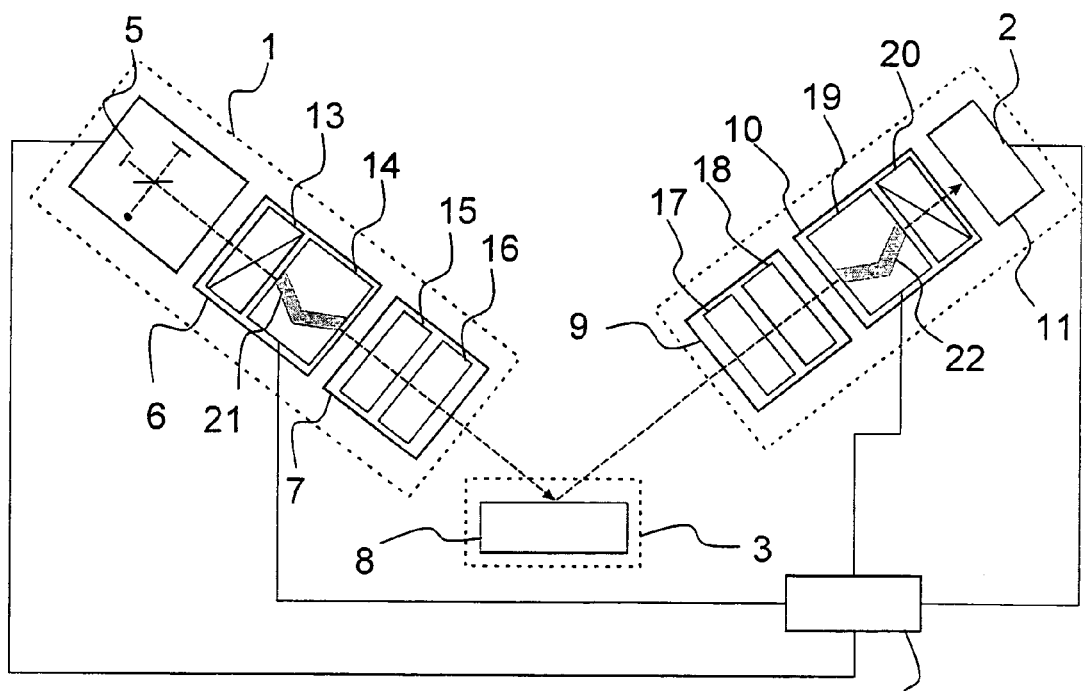
FIG. 13 is a schematic representation of another possible embodiment of the ellipsometer/polarimeter system optimized for the infrared, set in reflection configuration.

A second possible embodiment, represented in FIGS. 12 and 13, includes a broadband ellipsometer/polarimeter system working in the infrared that can be for example from 4 to 20 microns, but is not necessarily limited to this range.

According to FIGS. 12 and 13, the system, which can be used in transmission (FIG. 12) or in reflection (FIG. 13) mode, includes an input arm 1, a sample holder 3, an exit arm 2 and a computer 4. The input arm 1 includes an illumination source 5, a PSG 6 and a reference-sample-holder means 7.

The exit arm 2 includes a reference-sample-holder means 9, a PSA 10 and a primary detector system 11. The illumination source 5, such as a standard FTIR interferometer, provides a continuous infrared beam in a wide spectral range.

The PSG 6 comprises a fixed polarizer 13 located after the illumination source 5, and a substantially achromatic retarder 21. A preferred embodiment for the polarizer is the well known grid type, even if other types, like prisms, are also possible. Both retarders, 21 and 22 must be substantially achromatic, and provide a retardation close to 132°. In a preferred embodiment, retarder 21 must be either:
  a bi-prism 51 or,
  a retarder according to the description of the second substantially achromatic retarder 23', or
  a retarder according to the description of the third substantially achromatic retarder 23", or
  a retarder according to the description of the fourth substantially achromatic retarder 30', and the the retarder 22 must be:
  a bi-prism 51 or,
  a retarder according to the description of the second substantially achromatic retarder 23', or
  a retarder according to the description of the third substantially achromatic retarder 23", or
  a retarder according to the description of the fourth substantially achromatic retarder 30'.

The retarder 21 is mounted in a rotating holder 14, that allows it to be placed at four consecutive orientations respect to the plane of incidence. The rotating holder 14 can be rotated, manually or automatically, following a predetermined sequence controlled by the computer 4.

In a preferred embodiment, the rotating holder 14, is driven automatically by a motor connected to the computer 4 to ensure fast and repetitive movements. Holders 7, 9 for reference samples 15, 16, 17, 18, respectively, located after the PSG 6 and before the PSA 10, can introduce calibration samples 8 in the beam path during calibration, and remove them during current measurement process.

The PSA 10 include a fixed linear polarizer 20 and a substantially achromatic retarder 22 mounted on a rotating holder 19.

The beam goes through said PSA 10, after being transmitted, reflected or scattered by the sample 8.

The PSA 6 is identical to the PSG 10, but with its optical elements, (retarder and polarizer) set in reverse order.

We mean with "identical" that the PSG 6 and the PSA 10 comprise the same elements or equivalent elements having the same optical properties.

The rotating holders 14, 19 run in a stepper mode.

The computer 4 is intended to monitor the sequence of movements of the retarders 21, 22, either directly, or assisted by secondary specific controllers. In addition, the computer 4 has also in charge the control the FTIR source 5, the acquisition of raw data from the detection unit and its subsequent treatment.

According to the present invention, during the data acquisition, the retarder 21 in the PSG 6 is successively oriented at four defined angles $\theta_1$, $\theta_2$, $\theta_3$, and $\theta_4$, with $\theta_1$ being either 38° or 218°, $\theta_2$ being either 74° or 254°, $\theta_3$ being either 106° or 286° and $\theta_4$ being either 142° or 322°, to generate different polarization states that are sent to the sample. Each one of the four polarization states, after interacting with the sample, is projected against four optical configurations of the PSA 10, made by orienting retarder 22 at four different angles, $\theta_1$, $\theta_2$, $\theta_3$, and $\theta_4$, with $\theta_1$ being either 38° or 218°, $\theta_2$ being either 74° or 254°, $\theta_3$ being either 106° or 286° and $\theta_4$ being either 142° or 322°. The set of four selected orientation angles are optimized in order to maintain the condition numbers of the modulation and the analysis matrices associated respectively with the PSG 6 and the PSA 10 over 0.2.

As a result a set of sixteen $S_{i,j}$ measurements are obtained. The Mueller matrix of the sample 8 is obtained multiplying the matrix S by the inverse of the matrices W and A ($M = A^{-1} S W^{-1}$) corresponding the PSG 6 and the PSA 10 respectively.

The method chosen to calibrate the broadband ellipsometer/polarimeter system is based in the eigenvalue method described in the article of E. Compain {Appl. Opt., (1999)} because of its robustness. Apart from Compain et al, other authors like Drévillon et al. {U.S. Pat. No. 6,175,412 B1 and the Pub. No.: US 2004/0130717 A1} have already successfully applied the eigenvalue method to many kinds of polarimetric systems.

The eigenvalue method for calibration can be applied at the spectroscopic broadband systems according to the present invention.

As stated previously, the raw data given by the disclosed ellipsometer/polarimeter are equivalent to the matrix product AMW. To obtain M it is necessary to know a priori A and W. Even if the hypothesis of ideal elements can give a first approach, a calibration procedure is necessary in order to determine the real values of A and W that account for the effect of possible multiple-reflected beams, small defects, misalignment or imprecise orientation of the optical elements among other instrumental non-idealities.

The present calibration procedure is general and is valid for the calibration of the ellipsometer/polarimeter system set either in reflection or in transmission mode. According to the method and for clarity purposes, the experimental measurements are written in lower case, and the theoretical or ideal mathematical elements representing physical objects are noted in upper case. For two samples with Mueller matrices $M_1$ and $M_2$, the raw data resulting from their respective measurements are $(am_1 w)$ and $(am_2 w)$ and their respective theoretical raw data equivalents are $AM_1 W$ and $AM_2 W$. In absence of errors or noise, those expressions are related by:

$$\left. \begin{array}{l} AM_1 W = (am_1 w) \\ AM_2 W = (am_2 w) \end{array} \right\} \quad (10)$$

Considering that $M_1$ and W are invertible, it is possible to obtain A:

$$A = (am_1 w) W^{-1} M_1^{-1}$$

The substitution of the last expression in (10) results in the following:

$$M_1^{-1} M_2 W - W (am_1 w)^{-1} (am_2 w) = 0 \quad (11)$$

After a similar mathematical manipulation, but with W instead of A, one obtains:

$$AM_2 M_1^{-1} - (am_2 w)(am_1 w)^{-1} A = 0 \quad (12)$$

Equations 11 and 12 form a system of linear equations where A and W are the unknowns. However, up to this point nothing is known about the theoretical expressions $M_1^{-1}M_2$ and $M_2M_1^{-1}$. The eigenvalue method provides an original way to solve this apparent difficulty with the use of a simple set of calibration samples. For example, let's take a polarizer oriented to zero degree as a reference sample. The measurement of raw data without the polarizer gives $B_0=AM_0W$, where $M_0$ can correspond either to a mirror located in the sample-holder if the ellipsometer is set in reflection, or to the unit matrix if the polarimeter is set in transmission without a sample between the PSG and the PSA. To obtain W, the polarizer must be located between the PSG and the sample-holder, thus, giving a raw matrix $B_P=AM_0PW$, with P given by the expression 1. Multiplication of the inverse of $B_0$ by $B_P$ gives: $C_P=B_0^{-1}B_P=W^{-1}PW$. In theory, the eigenvalues of $C_P$ and P are the same. Knowing that P has only one non-zero eigenvalue $\lambda_1=2\tau_p$, then it is possible to perform a direct measurement of $\tau_P$ which is the sole parameter needed to characterize completely the matrix P. Back to expression 11, assuming that $M_1$ equals $M_0$, and that $M_2$ equals $M_0P$, the expression can be rewritten as:

$$PW-W(am_0w)^{-1}(am_0pw)=0 \qquad (13)$$

To obtain A, a similar operation must be done. Continuing with the example of the polarizer as a reference sample, it is now necessary to locate it between the sample-holder and the PSA. Again, two measurements have to be performed, one without the polarizer giving $B_0=AM_0W$, and another with the polarizer giving $B_P=APM_0W$. The product of $B_P$ by the inverse of $B_0$ gives: $C_P=B_PB_0^{-1}=A\,PA^{-1}$. Because the eigenvalues of $C_P$ and P are the same, it is possible to determine completely the matrix P. Now identifying $M_1$ with $M_0$ and $M_2$ with $PM_0$, it is possible to write the expression 12 in terms of P as follows:

$$AP-(apm_0w)(am_0w)^{-1}A=0 \qquad (14)$$

Expressions 13 and 14 are now well defined equations. One of the possible ways to solve 13 and 14 consists of using an algebraic method. First, let's to create two linear mappings or applications, $H^W$ and $H^A$, from the space of four-dimensional real matrices, $\{R^{4\times 4}\}$ to itself $\{R^{4\times 4}\}$, having the following expressions:

$$H^W(X)=PX-X(am_0w)^{-1}(am_0pw) \qquad (15)$$

$$H^A(X)=XP-(apm_0w)(am_0w)^{-1}X \qquad (16)$$

As any linear mapping, $H^W$ and $H^A$ have a defined kernel and they can be represented by a matrix. Briefly, the kernel of a mapping is defined as the set of elements mapped towards the null element. The dimension of the kernel corresponds to the number of linearly independent elements in the set. By virtue of expressions 11 and 12, the matrix W belongs to the kernel of $H^W$ and the matrix A to the kernel of $H^A$. When singular value decomposition (SVD) is performed on the matrix associated to a given mapping, a diagonal matrix can be obtained with a number of null diagonal elements equal to the dimension of the kernel. Further, it is known that each null singular value has an associated singular vector that turns out to be proportional to one of the elements of the kernel. Accordingly, if the kernel of $H^W$ and that of $H^A$ are of dimension 1, each of the corresponding associated matrices will have a unique null singular value with an associated singular vector being proportional to the desired solution W and A respectively, and the calibration problem will be solved. However, in practice, two difficulties arise. Firstly, W and A are matrices and not vectors, and secondly, if a polarizer or a retarder is used alone as unique reference sample, the dimension of the kernel cannot be one. The first difficulty is only apparent because the difference between vectors and matrices is only formal. In fact, the 4×4 matrices appearing in expressions 15 and 16 can be rewritten in the form of 16-dimensional vectors by taking the four columns of the matrix and writing them, one below the other, under the form a column that can be manipulated like a vector. Using 16-dimensional vectors, the mappings $H^W$ and $H^A$ can be represented by the 16×16 associate matrices $H^W$ and $H^A$ respectively. On the other hand, the dimension of the kernel of $H^W$ and $H^A$ can be reduced to one if a set of reference samples are used instead of only a single sample. In the most general case, where a number "n" of samples have to be used, the following "n" mappings can be built for the PSG and the PSA respectively:

$$H_i^W(X)=M_iX-X(am_0w)^{-1}(am_0m_iw) \qquad (17)$$

$$H_i^A(X)=XM_i-(am_im_0w)(am_0w)^{-1}X \qquad (18)$$

Where $M_i$ (i=1 ... n) are the Mueller matrices of the n reference samples. Finding W or A is equivalent to find the solution of the following over-determined systems of equations:

$$H_i^W(W)=M_iW-W(am_0w)^{-1}(am_0m_iw)=H_i^WW=0 \qquad (19)$$

$$H_i^A(A)=AM_i-(am_im_0w)(am_0w)^{-1}A=H_i^AA=0 \qquad (20)$$

The solution of an over-determined linear system by least-squares method is given by the well-know relation {W. H. Press, B. P. Flannery, Numerical recipes in PASCAL}:

$$K_i^WW=0 \qquad (21)$$

$$K_i^AA=0 \qquad (22)$$

Where:

$$K_i^W = \begin{pmatrix} H_1^W \\ \vdots \\ H_n^W \end{pmatrix}^T \begin{pmatrix} H_1^W \\ \vdots \\ H_n^W \end{pmatrix} = (H_1^W)^T H_1^W + \cdots + (H_n^W)^T H_n^W = 0 \qquad (23)$$

$$K_i^A = \begin{pmatrix} H_1^A \\ \vdots \\ H_n^A \end{pmatrix}^T \begin{pmatrix} H_1^A \\ \vdots \\ H_n^A \end{pmatrix} = (H_1^A)^T H_1^A + \cdots + (H_n^A)^T H_n^A = 0 \qquad (24)$$

The matrices $K_i^W$ and $K_i^A$ are symmetrical and definite positive so, they can be diagonalized. Both matrices have only one null eigenvalue with a related eigenvector being proportional to W, and A respectively.

The type and the number of calibration samples is not unique. A reasonable choice consists of using the minimum number of elements. In that way, it has been demonstrated that a pair of polarizers combined with a retarder, or alternatively, two retarders together with a polarizer, can be conveniently used as calibration samples sets. The characteristics of the first set are:

A linear polarizer oriented at −20° with respect to the incidence plane.

A linear polarizer oriented at +40° with respect to the incidence plane.

A linear retarder providing retardation between 30 and 170°, oriented parallel to the incidence plane.

The characteristics of the second set of calibration samples are:

A linear polarizer oriented at −20° with respect to the incidence plane.

A linear retarder providing retardation between 30° and 170° oriented at +40° with respect to the incidence plane.

A linear retarder providing retardation between 30° and 170°, oriented parallel with respect to the incidence plane.

The invention claimed is:

1. A broadband ellipsometer/polarimeter system for analysing a sample (8) comprising:
   an illumination source (5) emitting a polychromatic light beam (12),
   a polarisation state generator (PSG) (6) including a fixed linear polarizer (13) and a substantially achromatic retarder (21) mounted on a rotating holder (14), said light beam (12) passing through said PSG (6),
   a sample holder (3), on which the sample (8) can be mounted, the light beam (12) being focused on the sample (8),
   a polarisation state analyser (PSA) (10) including a fixed linear polarizer (20) and a substantially achromatic retarder (22) mounted on a rotating holder (19), the beam going through said PSA (10), after being transmitted, reflected or scattered by the sample (8),
   a primary detection system (11) measuring the intensity of the light beam transmitted through said PSA (10) at each wavelength,
   optics to collimate the beam into the PSG (6) and into the PSA (10) and to focus the beam into the sample surface,
   wherein,
   said linear polarizer (20) and said substantially achromatic retarder (22) in the PSA (10) are identical to the linear polarizer (13) and the substantially achromatic retarder (21) of the PSG (6) and inverted according to the sense of propagation of the light,
   said rotating holders (14, 19) run in a stepper mode allowing a set of only four selected orientation angles for the retarders (21, 22), said set of four selected orientation angles being optimized in order to maintain the condition numbers of the modulation and analysis matrices associated respectively with the PSG (6) and the PSA (10) over 0.2.

2. A broadband ellipsometer/polarimeter system according to claim 1, characterised in that the substantially achromatic retarder (21) of the PSG (6) are total internal reflection based retarder providing a phase-shift of either $\{132°\pm30°+n360°\}$ or $\{227°\pm30°+n360°\}$ for all the wavelengths of the light beam (12), with "n" being any integer.

3. A broadband ellipsometer/polarimeter system according to claim 1, characterised in that the substantially achromatic retarder (22) of the PSA (10) are total internal reflection based retarder providing a phase-shift of either $\{132°\pm30°+n360°\}$ or $\{227°\pm30°+n360°\}$ for all the wavelengths of the light beam (12), with "n" being any integer.

4. A broadband ellipsometer/polarimeter system according to claim 1, characterized in that the substantially achromatic retarder (21) of the PSG (6) is placed at a set of four selected orientation angles $\theta_1, \theta_2, \theta_3$ and $\theta_4$, said $\theta_1$ being either $\{38\pm20°+n360°\}$ or $\{218\pm20°+n360°\}$, said $\theta_2$, being either $\{75\pm20°+n360°\}$ or $\{255\pm20°+n360°\}$, said $\theta_3$ being either $\{104\pm20°+n360°\}$ or $\{284\pm20°+n360°\}$, and said $\theta_4$ being $\{142\pm20° +n360°\}$ or $\{322\pm20°+n360°\}$, with "n" being any integer.

5. A broadband ellipsometer/polarimeter system according to claim 1, characterized in that the substantially achromatic retarder (22) of the PSA (10) is placed at four selected orientation angles $\theta_1, \theta_2, \theta_3$ and $\theta_4$, said $\theta_1$ being either $\{38\pm20°+n360°\}$ or $\{218\pm20°+n360°\}$, said $\theta_2$, being either $\{75\pm20°+n360°\}$ or $\{255\pm20°+n360°\}$, said $\theta_3$ being either $\{104\pm20°+n360°\}$ or $\{284\pm20°+n360°\}$, and said $\theta_4$ being $\{142\pm20° +n360°\}$ or $\{322\pm20°+n360°\}$, with "n" being any integer.

6. A broadband ellipsometer/polarimeter system according to claim 1, characterised in that the substantially achromatic retarder (21) of the PSG (6) comprises at least two prisms, said substantially achromatic retarder (21) causing at least four internal reflections to the light beam (12) entering on it and said beam (12) is not deviated.

7. A broadband ellipsometer/polarimeter system according to claim 1, characterised in that the substantially achromatic retarder (22) of the PSA (10) comprises at least two prisms, said substantially achromatic retarder (22) causing at least four internal reflections to the light beam (12) entering on it and said beam (12) is not deviated.

8. A broadband ellipsometer/polarimeter system according to claim 6, characterised in that the substantially achromatic retarder (21) of the PSG (6) is a bi-prism (51) in "V" shape, each bi-prism (51) consists of two rhombs (50, 50') having an identical shape, optically assembled by one of their sides.

9. A broadband ellipsometer/polarimeter system according to claim 7, characterised in that the substantially achromatic retarder (22) of the PSA (10) is a bi-prism (51) in "V" shape, each bi-prism (51) consists of two rhombs (50, 50') having an identical shape, optically assembled by one of their sides.

10. A broadband ellipsometer/polarimeter system according to claim 6, characterised in that the substantially achromatic retarder (21) of the PSG (6) comprises three triangular prisms (24, 25, 26) from which, at least two have an identical shape.

11. A broadband ellipsometer/polarimeter system according to claim 7, characterised in that the substantially achromatic retarder (22) of the PSA (10) comprises three triangular prisms (24, 25, 26) from which, at least two have an identical shape.

12. A broadband ellipsometer/polarimeter system according to claim 6, characterised in that the substantially achromatic retarder (21) of the PSG (6) comprises three prisms (27, 28, 29), two prisms (27, 29) of said three prisms (27, 28, 29) are triangular and one prism (28) is trapezoidal.

13. A broadband ellipsometer/polarimeter system according to claim 7, characterised in that the substantially achromatic retarder (22) of the PSA (10) comprises three prisms (27, 28, 29), two prisms (27, 29) of said three prisms (27, 28, 29) are triangular and one prism (28) is trapezoidal.

14. A broadband ellipsometer/polarimeter system according to claim 6, characterised in that the substantially achromatic retarder (21) of the PSG (6) comprises four trapezoidal prisms (31, 32, 33, 34) having an identical shape.

15. A broadband ellipsometer/polarimeter system according to claim 7, characterized in that the substantially achromatic retarder (22) of the PSA (10) comprises four trapezoidal prisms (31, 32, 33, 34) having an identical shape.

16. A broadband ellipsometer/polarimeter system according to claim 6, characterised in that each prism is made of a material with an index of refraction greater than that of the surrounding media.

17. A broadband ellipsometer/polarimeter system according to claim 6, characterised in that the entrance and exit faces of the prisms comprise an antireflection treatment (coating) to minimise light insertion losses.

18. A broadband ellipsometer/polarimeter system according to claim 6, characterised in that the faces of the prisms wherein total internal refection takes place, are uncoated.

19. A broadband ellipsometer/polarimeter system according to claim 6, characterised in that the prisms of the substantially achromatic retarders (21, 22) are made of a material presenting a low index of refraction like the $BaF_2$.

20. A broadband ellipsometer/polarimeter system according to claim 1, characterised in that the primary detection system (11) measures simultaneously the intensity of all the wavelengths of the light beam transmitted through said PSA (10).

21. A broadband ellipsometer/polarimeter system according to claim 1, characterised in that the primary detection system (11) measures simultaneously and separately the intensity of each wavelength of the light beam transmitted through said PSA (10).

22. A broadband ellipsometer/polarimeter system according to claim 1, characterised in that it includes a secondary detection system (32) to monitor the power given by the illumination source (5) including a beam-splitter (23) located between the illumination source (5) and the PSG (6) and a secondary detector (24).

23. A broadband ellipsometer/polarimeter system according to claim 1, characterised in that it includes a holder for reference samples (7), said holder is placed between the PSG (6) and the sample holder (3), said holder introduce a set reference samples (15), (16) in the beam path (12) during calibration, and remove them during measurement process.

24. A broadband ellipsometer/polarimeter system according to claim 1, characterised in that it includes a holder for reference samples (9), said holder is placed between the sample holder (3) and the PSA (10), said holder introduce a set reference samples (17), (18) in the beam path (12) during calibration, and remove them during measurement process.

25. A broadband ellipsometer/polarimeter system according to claim 1, characterised in that said system operates in a spectral range from 4 to 20 microns.

26. A broadband ellipsometer/polarimeter system according to claim 1, characterised in that said system operates in a FUV-NIR spectral range from 140 nm to 2000 nm.

* * * * *